United States Patent
Lee et al.

[11] Patent Number: 6,113,866
[45] Date of Patent: Sep. 5, 2000

[54] APPARATUS FOR PREPARING PURIFIED TEREPHTHALIC ACID

[75] Inventors: Fu-Ming Lee; Wiston Lamshing, both of Katy, Tex.

[73] Assignee: HFM International, Inc., Clinton, N.J.

[21] Appl. No.: 09/436,786

[22] Filed: Nov. 8, 1999

Related U.S. Application Data

[60] Division of application No. 08/760,890, Dec. 6, 1996, Pat. No. 6,013,835, which is a continuation-in-part of application No. 08/477,898, Jun. 7, 1995, Pat. No. 5,767,311.

[51] Int. Cl.$^7$ .................................................. B01D 9/02
[52] U.S. Cl. ........................................................ 422/245.1
[58] Field of Search ........................................... 422/245.1

[56] References Cited

U.S. PATENT DOCUMENTS

| | | | |
|---|---|---|---|
| 2,636,899 | 4/1953 | Burrows et al. | 562/410 |
| 2,811,548 | 10/1957 | Ham et al. | 562/432 |
| 2,829,160 | 4/1958 | Stehman et al. | 562/480 |

(List continued on next page.)

FOREIGN PATENT DOCUMENTS

| | | |
|---|---|---|
| 611607 | 6/1962 | Belgium . |
| 614720 | 9/1962 | Belgium . |
| 615996 | 10/1962 | Belgium . |
| 732838 | 10/1969 | Belgium . |
| 1316914 | 2/1963 | France . |
| 1117100 | 11/1961 | Germany . |
| 818211 | 8/1959 | United Kingdom . |
| 881460 | 3/1960 | United Kingdom . |
| 849189 | 9/1960 | United Kingdom . |
| 908011 | 10/1962 | United Kingdom . |
| 1049720 | 11/1966 | United Kingdom . |
| 1290981 | 9/1972 | United Kingdom . |

OTHER PUBLICATIONS

Tr. Vses. Nauch.–Issled. Proekt. Inst. Monomerov (1970), 2(2), 26–32; From: Ref. Zh., Khim. 1971, Abstr. No. 1N166; V.N. Kulakov, et al.; "Purification of Aromatic Dicarboxylic Acids Obtained by Liquid–Phase Oxidation of Dialkyl Derivatives of Aromatic Hydrocarbons".

Abstract—Database WPI XP–002063355, Section CH, Derwent Publications Ltd., London, GB; Class A41, Appl. No. 96–017160, Pat. No. JP7291896; Mitsubishi Gas Chem. Co., Inc., "Preparation of High–Purity Terephthalic Acid" (Nov. 1995).

Abstract—Database WPI XP–002063356, Section CH, Derwent Publications Ltd., London, GB; Class A41, Appl. No.72/77189T, Pat. No. JP47046663B; Toray Ind., Inc., "Crystallization Process for Purification of Materials Containing Trace Impurities".

*Primary Examiner*—Benjamin L. Utech
*Assistant Examiner*—Donald L. Champagne
*Attorney, Agent, or Firm*—Jenkins & Gilchrist, A Professional Corporation

[57] ABSTRACT

A method and apparatus for purifying crude terephthalic acid from a liquid dispersion thereof also containing impurities selected from unreacted starting materials, solvents, products of side reactions and/or other undesired materials is provided. The method comprises the steps of filtering the dispersion to form a crude terephthalic acid filter cake, dissolving the filter cake in a selective crystallization solvent at an elevated temperature to form a solution, crystallizing purified terephthalic acid from the solution in the crystallization solvent by reducing the pressure and temperature of the solution, and separating the crystallized purified terephthalic acid from the solution. According to the invention, the selective crystallization solvent is non-aqueous, non-corrosive and essentially non-reactive with terephthalic acid. Preferably, the selective crystallization solvent is N-methyl pyrrolidone. The method and apparatus produces purified terephthalic acid having a purity desired for use in forming polyester resin and other products at an economically attractive rate and at operating conditions of reduced severity which require a lower capital investment and simplified processing.

3 Claims, 3 Drawing Sheets

U.S. PATENT DOCUMENTS

| | | | |
|---|---|---|---|
| 2,833,816 | 5/1958 | Saffer et al. | 562/416 |
| 2,833,817 | 5/1958 | Saffer et al. | 562/414 |
| 2,849,483 | 8/1958 | Ham et al. | 562/471 |
| 2,891,992 | 6/1959 | Raecke et al. | 562/481 |
| 2,905,709 | 9/1959 | Schenk et al | 562/482 |
| 2,923,736 | 2/1960 | Maclean et al. | 562/485 |
| 2,949,483 | 8/1960 | Ham | 562/432 |
| 3,330,863 | 7/1967 | Read et al. | 562/485 |
| 3,388,156 | 6/1968 | Sakurai et al. | 562/485 |
| 3,465,035 | 9/1969 | Nakaguchi et al. | 562/486 |
| 3,574,727 | 4/1971 | Taylor et al. | 562/487 |
| 3,584,039 | 6/1971 | Meyer | 562/486 |
| 3,859,344 | 1/1975 | Shigeyasu et al. | 562/414 |
| 3,862,218 | 1/1975 | Stautzenberger | 562/486 |
| 3,887,613 | 6/1975 | Blay | 562/486 |
| 3,899,530 | 8/1975 | Syoji et al. | 562/486 |
| 3,931,305 | 1/1976 | Fisher | 562/486 |
| 3,953,502 | 4/1976 | Fassell et al. | 562/483 |
| 4,053,506 | 10/1977 | Park et al. | 562/414 |
| 4,081,464 | 3/1978 | Marsh et al. | 562/414 |
| 4,165,337 | 8/1979 | Yoshinaka et al. | 562/855 |
| 4,197,412 | 4/1980 | Kimura et al. | 562/416 |
| 4,201,782 | 5/1980 | Narisada et al. | 514/210 |
| 4,201,871 | 5/1980 | Tanouchi et al. | 562/486 |
| 4,201,872 | 5/1980 | Kimura et al. | 562/487 |
| 4,228,299 | 10/1980 | Ferguson et al. | 560/124 |
| 4,230,882 | 10/1980 | Seko et al. | 562/416 |
| 4,245,078 | 1/1981 | Suzuki et al. | 562/412 |
| 4,260,817 | 4/1981 | Thompson et al. | 562/487 |
| 4,263,452 | 4/1981 | Komatsu et al. | 562/487 |
| 4,268,690 | 5/1981 | Komatsu et al. | 562/416 |
| 4,275,230 | 6/1981 | Donaldson | 562/486 |
| 4,281,179 | 7/1981 | Komatsu et al. | 562/416 |
| 4,286,101 | 8/1981 | Hashizume et al. | 562/416 |
| 4,297,507 | 10/1981 | Komatsu et al. | 562/416 |
| 4,314,073 | 2/1982 | Crooks | 562/416 |
| 4,317,923 | 3/1982 | Imai | 562/487 |
| 4,331,824 | 5/1982 | Ikeda et al. | 585/638 |
| 4,334,090 | 6/1982 | Donaldson | 562/480 |
| 4,340,752 | 7/1982 | List et al. | 562/485 |
| 4,345,089 | 8/1982 | Nagura et al. | 560/77 |
| 4,357,475 | 11/1982 | Hanotier et al. | 562/414 |
| 4,380,662 | 4/1983 | Hanotier et al. | 562/486 |
| 4,415,479 | 11/1983 | Puskas et al. | 502/85 |
| 4,438,279 | 3/1984 | Packer et al. | 562/146 |
| 4,447,646 | 5/1984 | Johnson et al. | 562/487 |
| 4,459,718 | 7/1984 | Greenshields | 549/370 |
| 4,467,110 | 8/1984 | Puskas et al. | 562/487 |
| 4,467,111 | 8/1984 | Puskas et al. | 562/487 |
| 4,485,244 | 11/1984 | Fox et al. | 549/245 |
| 4,490,554 | 12/1984 | Tanaka et al. | 562/486 |
| 4,500,732 | 2/1985 | Petty-Weeks et al. | 562/486 |
| 4,537,980 | 8/1985 | Greenshields | 549/370 |
| 4,540,493 | 9/1985 | Dickerson et al. | 210/669 |
| 4,605,763 | 8/1986 | Kiefer et al. | 502/487 |
| 4,625,059 | 11/1986 | Shibano et al. | 562/600 |
| 4,626,598 | 12/1986 | Packer et al. | 562/487 |
| 4,629,715 | 12/1986 | Schroeder | 502/185 |
| 4,652,674 | 3/1987 | James et al. | 562/414 |
| 4,675,108 | 6/1987 | Dickerson et al. | 210/275 |
| 4,675,438 | 6/1987 | Schwartz et al. | 562/416 |
| 4,728,630 | 3/1988 | Schroeder et al. | 502/185 |
| 4,772,748 | 9/1988 | Hashizume et al. | 562/413 |
| 4,782,181 | 11/1988 | James | 562/487 |
| 4,791,226 | 12/1988 | Puskas et al. | 562/487 |
| 4,808,751 | 2/1989 | Schroeder et al. | 562/487 |
| 4,827,026 | 5/1989 | Brugg et al. | 562/416 |
| 4,833,269 | 5/1989 | Schroeder | 562/484 |
| 4,877,900 | 10/1989 | Tamaru et al. | 562/413 |
| 4,892,972 | 1/1990 | Schroeder et al. | 562/487 |
| 4,933,491 | 6/1990 | Albertins et al. | 562/416 |
| 4,933,492 | 6/1990 | Schroeder et al. | 562/487 |
| 4,937,378 | 6/1990 | Schroeder | 562/467 |
| 4,939,297 | 7/1990 | Browder et al. | 562/483 |
| 4,948,921 | 8/1990 | Green et al. | 562/413 |
| 5,068,410 | 11/1991 | Tanaka et al. | 562/483 |
| 5,095,144 | 3/1992 | Sato et al. | 562/481 |
| 5,095,145 | 3/1992 | Rosen | 562/483 |
| 5,095,146 | 3/1992 | Zeitlin et al. | 562/486 |
| 5,097,066 | 3/1992 | Holzhauer et al. | 562/487 |
| 5,107,020 | 4/1992 | Reeve | 562/416 |
| 5,110,984 | 5/1992 | Janulis | 562/487 |
| 5,159,109 | 10/1992 | Rosen et al. | 562/509 |
| 5,166,420 | 11/1992 | Shiraki et al. | 562/487 |
| 5,169,977 | 12/1992 | Tanaka et al. | 560/78 |
| 5,175,352 | 12/1992 | Iwane et al. | 562/417 |
| 5,175,355 | 12/1992 | Streich et al. | 562/485 |
| 5,175,358 | 12/1992 | Capai et al. | 562/537 |
| 5,183,933 | 2/1993 | Harper et al. | 562/414 |
| 5,189,209 | 2/1993 | Ohta et al. | 562/414 |
| 5,200,557 | 4/1993 | Gee et al. | 562/486 |
| 5,254,719 | 10/1993 | Holzhauer et al. | 560/78 |
| 5,306,845 | 4/1994 | Yokohama et al. | 562/484 |
| 5,344,969 | 9/1994 | Iwane et al. | 562/486 |
| 5,354,898 | 10/1994 | Schroeder | 562/485 |
| 5,362,908 | 11/1994 | Schroeder | 562/487 |
| 5,563,293 | 10/1996 | Hindmarsh et al. | 562/414 |
| 5,567,842 | 10/1996 | Izumisawa et al. | 562/486 |
| 5,767,311 | 6/1998 | Lee et al. | 562/487 |
| 6,013,835 | 1/2000 | Lee et al. | 562/487 | ly, 
APPARATUS FOR PREPARING PURIFIED TEREPHTHALIC ACID

This application is a divisional of application Ser. No. 08/760,890, filed Dec. 6, 1996, U.S. Pat. No. 6,013,835, which is a continuation-in-part of application Ser. No. 08/477,898, filed Jun. 7, 1995, U.S. Pat. No. 5,767,311.

This application is a continuation-in-part of co-pending application Ser. No. 08/477,898, filed Jun. 7, 1995, entitled Method and Apparatus for Preparing Purified Terephthalic Acid, which is assigned to the same assignee as this application, and the totality of the disclosure of which is hereby incorporated by reference for all purposes.

The present invention relates to a method and apparatus for preparing purified terephthalic acid. It also relates to methods and apparatuses for purifying crude terephthalic acid to produce a purified terephthalic acid product which is a useful starting material for producing polyester resin, which is in turn useful for the production of fibers, film, plastic bottles, and polyester resin structures, often reinforced by other materials such as glass fiber.

BACKGROUND OF THE INVENTION

Purified terephthalic acid (PTA) is a starting material for the formation of polyester resin, which is, in turn, used to make many materials of commerce having a variety of utilities. Purified terephthalic acid is formed from "crude" terephthalic acid conventionally by a number of purification methods, often with the aid of catalysts. The methods for purifying crude terephthalic acid heretofore available are not completely satisfactory either from an engineering standpoint, or from an economic standpoint, yet the purity of the purified terephthalic acid is an important determinant of the satisfactoriness of the processes by which the polyester resin is formed.

A number of reaction systems are known for forming crude terephthalic acid from a variety of starting materials. The purification aspects of the present invention may be used with substantially any of these reaction systems, but in accordance with the invention it is preferred that a reaction system involving the oxidation of paraxylene (p-xylene) be employed, and the use of such a synthesis system forms a part of the present invention.

The problems of existing and prior systems for producing purified terephthalic acid center around the difficulties in running the reaction systems to produce good yields of crude terephthalic acid economically, compounded by the difficulties of refining the crude terephthalic acid to eliminate impurities and unwanted components to produce purified terephthalic acid of a quality suitable as a starting material for producing polyester. Concomitant problems in prior systems include the high capital investment required for PTA plants, the severity of operating conditions of prior processes, both for the production of crude terephthalic acid, and for its purification, and the need for handling catalyst systems and reaction solvents, as well as reaction byproducts in a way such that environmental problems are minimized, and loss of material is also controlled.

One factor of importance in the production of purified terephthalic acid is the formation of crystals having a size and shape giving them good handling characteristics, washability and filterability.

SUMMARY OF THE INVENTION

In accordance with the present invention there is provided a method and apparatus for producing purified terephthalic acid. In one aspect, the method includes the production of crude terephthalic acid by the oxidation of p-xylene. The oxidation step produces not only terephthalic acid, but by side reactions p-toluic acid and 4-carboxybenzaldehyde (4-CBA). The product produced in the oxidation step is a liquid dispersion containing unreacted starting materials, solvents, if any have been used, the products of side reactions, particularly those just mentioned, and other materials which are not desired in the sought-for purified terephthalic acid. The oxidation step of the present invention is so conducted that the conversion to crude terephthalic acid should be at least about 30% by weight per pass of p-xylene.

In further accordance with the invention, the crude terephthalic acid from the oxidizer is first grossly separated from the other materials from the oxidizer and then it is re-dissolved in a selective crystallization solvent and, optionally, one or more additional solvents of the invention discussed below. The re-dissolved crude terephthalic acid is then crystallized out of the selective crystallization solvent and additional solvents of the invention in one or, preferably, two crystallization stages. Provision is made to separate out the crystallized and progressively purified terephthalic acid from the solvents of the invention, and the filter cake of purified terephthalic acid ultimately obtained is washed with other solvents of the invention and dried or, alternatively, dried (e.g., using a vacuum dryer), sent to a soaker to remove residual solvent, and ultimately filtered and dried for storage or for further processing.

Also in accordance with the present invention, improvements in the crystallization processes just outlined are provided which produce larger more globular crystals that are thought to contain little or no salt of the kind which may tend to form when the selective crystallization solvent(s) is an organic base. The larger non-salt crystals have the advantage that they resist destruction by water rinsing and are otherwise easier to recover solvent from, as well as being easier to rinse for removal of residual impurities.

The improvements in the crystallization processes comprise flashing solvent from the crystallizing acid by reducing the pressure on it, preferably both prior to and during the cooling of the saturated acid solution. It is further preferred to reduce the pressure progressively to lower levels, either in a batch or continuous flow crystallizer, and this may be arranged to be performed stepwise or continuously. Still further, heat may be added to the crystallizing acid during the application of reduced pressure to increase the rate and quantity of solvent removal, care being taken, however, to avoid materially increasing the temperature of the crystallizing acid to cause redissolution of the acid and consequent waste of energy.

As was mentioned above, in accordance with the invention, crystallization may be performed in multiple stages; when this form of the invention is used, it is preferred that some or all of the crystallization improvement techniques just discussed be utilized in the second or last stage, although the techniques may also be used to advantage in the first stage.

Further in accordance with the invention, co-solvents may be used for purifying terephthalic acid by flash crystallization. A co-solvent having a lower boiling point than the solvent can be used to reduce the flashing temperature for crystallization and hence the dissolution temperature. With a lower flashing temperature, crystallization can be carried out under a lower degree of vacuum.

The co-solvents include water, $C_1$ to $C_5$ alcohols, such as methanol or ethanol, $C_5$ to $C_{10}$ hydrocarbons, such as p-xylene, and $C_1$ to $C_{10}$ organic acids, such as formic acid or acetic acid, etc. It is thus possible to include about 1 to about 50% inert solvents having boiling points ranging from 25 to 200° C. as the co-solvents.

The invention also contemplates that steps are included to reclaim and recycle the solvents of the invention at each stage of crystallization and washing, including recycle of some of the recovered materials to the oxidizer. Steps are also taken to closely control the delivery of any objectionable materials to the environment.

In an important aspect, the present invention is based on several discoveries relating to solvents which are effective to bring about the purification of crude terephthalic acid through crystallization and separation steps. These discoveries may be summarized in several ways as follows.

The selective crystallization solvents useful in the practice of the present invention include those in which (a) the impurities desired to be separated from terephthalic acid to purify it are relatively more soluble in the solvent than is the terephthalic acid at substantially every temperature within the desired range of temperatures at which the solvent containing terephthalic acid is to be handled, and (b) the terephthalic acid is more soluble at an elevated temperature and less soluble at a lower or reduced temperature. It is to be understood that the term "selective crystallization solvent" is intended to mean solvents useful in the selective crystallization of terephthalic acid as described above and as described in greater detail below and as shown in FIGS. 1 and 2.

In this connection it should be noted that U.S. Pat. No. 3,465,035 mentions that certain organic solvents (pyridine, dimethyl sulfoxides, dimethyl foramide, and the like) have been used to purify terephthalic acid, but that they suffer from being unstable in air and easily form addition products with terephthalic acid. This same patent, along with several others, also teaches the use of acetic acid and water as purification solvents for terephthalic acid. By contrast, the selective crystallization solvents according to the present invention are (a) non-aqueous, (b) non-corrosive, and (c) essentially non-reactive with terephthalic acid and do not include those prior practices just described. Specifically, water, acetic (and other alkyl) acid, and the above-mentioned organic solvents are excluded from the selective crystallization solvents which are contemplated by the present invention.

In accordance with the invention, the primary preferred selective crystallization solvents are N-methyl pyrrolidone (NMP) and N,N-dimethyl acetamide (DMAC), for the several reasons discussed below, and for their superior performance. U.S. Pat. No. 2,949,483, dated Aug. 16, 1960 to Ham, discloses NMP used to crystallize terephthalic acid, but does not use the same dissolution temperature range as in the present invention. Nor does it suggest flash crystallization or its advantageous results. Tr. Vses. Nauch.-Issled. Proekt. Inst. Monomerov (1970), 2(2), 26–32; From: Ref. Zh., Khim. 1971, Abstr. No. 1N166; V. N. Kulakov, et al.; entitled "Purification of Aromatic Dicarboxylic Acids Obtained by Liquid-Phase Oxidation of Dialkyl Derivatives of Aromatic Hydrocarbons," very briefly mentions NMP as a solvent, but says nothing about dissolution temperatures or flash crystallization.

N-methyl pyrrolidone (NMP) and N,N-dimethyl acetamide (DMAC) are the preferred selective crystallization solvents for the practice of the invention. These solvents are non-aqueous, thermally stable, non-toxic (environmentally safe), non-corrosive, and commercially available. NMP is the most preferred selective crystallization solvent for the practice of the present invention, because its solubility versus temperature curve for terephthalic acid slopes upwardly and to the right, which means that terephthalic acid can be dissolved in it at elevated temperatures, and precipitated or crystallized from it at lower temperatures.

Although NMP is the most preferred selective crystallization solvent, it is to be understood that DMAC exhibits similar desirable characteristics and that, in accordance with the present invention, other preferred selective crystallization solvents for purification of crude terephthalic acid can be selected from various polar organic solvents including, but not intended to be limited to, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), and N-hydroxyalkyl-2-pyrrolidone (such as N-hydroxyethyl-2-pyrrolidone), N-ethyl pyrrolidone, N-mercaptoethyl pyrrolidone, N-methyl thiopyrrolidone, N-hydroxyethyl pyrrolidone, 1,5-dimethyl pyrrolidone, N-methyl piperidone, N-methyl caprolactam, N-formyl morpholine, morpholine, N,N-dimethyl formamide, N,N-dimethyl acetamide, and N-formyl piperidine, and the like, and mixtures thereof. Still other selective crystallization solvents contemplated by the present invention include, but are not intended to be limited to, sulfolane, methyl sulfolane, the sulfones, the morpholines (such as, morpholine and N-formyl morpholine), the carbitols, $C^1$ to $C^{12}$ alcohols, the ethers, the amines, the amides, and the esters, and the like, and mixtures thereof.

It is preferred that the desired selective crystallization solvent be used in a multi-stage crystallization process in combination with one or more additional solvents, preferably two such additional solvents, particularly where the crude terephthalic acid is less than about 98% pure. Preferably, a wash solvent, such as, but not intended to be limited to, water, p-xylene, acetone, methyl ethyl ketone (MEK) or methanol, and the like, is used in the washing of the initial filter cake obtained from the first separation of crude terephthalic acid from other materials issuing from the oxidizer. In addition, a displacement solvent having a low boiling point, such as, but not intended to be limited to, water, methanol, acetone, MEK, and the like, may be used. Preferably, water is used as the displacement solvent in association with the third filter following the second crystallization stage in the preferred process. The desired displacement solvent displaces the selective crystallization solvent from the resulting filter cake, whereby substantially only the displacement solvent is present during the soaking process. The soaking process is preferred to eliminate any possible residual solvent trapped in the TA crystals before the product is subjected to the final filtration and drying steps.

As described above, NMP and DMAC are the preferred selective crystallization solvents for the practice of the invention. They are non-aqueous, thermally stable, non-toxic (environmentally safe), non-corrosive, and commercially available. NMP is the preferred selective crystallization solvent for the practice of the present invention, because, among other things, its solubility versus temperature curve for terephthalic acid slopes upwardly and to the right, which means that terephthalic acid can be dissolved in it at elevated temperatures, and precipitated or crystallized from it at lower temperatures. However, the solubility versus temperature curve for terephthalic acid is of a much milder slope than the solubility curves in NMP for other materials sought to be separated from crude terephthalic acid, such as benzoic acid, 4-carboxybenzaldehyde (4-CBA), and p-toluic acid. As a consequence, when crude terephthalic acid, containing or associated with unreacted starting materials, solvents (if any), and products of side reactions, such as those mentioned above, or other undesired materials, is dissolved in NMP or DMAC at an elevated temperature, substantially all the materials are dissolved or at least highly dispersed. Then upon removal of heat and pressure and subsequent cooling of the NMP or DMAC solution of such dissolved materials, the pure terephthalic acid preferentially crystallizes out, while the other more soluble materials which may be regarded as impurities for the present purposes remain in solution in NMP or DMAC. A separation is thus effected between purified terephthalic acid and its associated impurities. NMP or DMAC may be stripped of the impurities in a reclaiming column and recycled into the process, while the impurities may be recycled to the oxidizer step or otherwise disposed of.

From the foregoing, it can be seen that in accordance with one aspect of the present invention, a method is provided for producing purified terephthalic acid from crude terephthalic acid in which the crude terephthalic acid is dissolved in a desired crystallization solvent at an elevated temperature to form a solution and further, in which a purified terephthalic acid is crystallized from that solution at a reduced pressure and temperature.

In accordance with another aspect of the invention, a method and apparatus are provided for purifying crude terephthalic acid from a liquid dispersion thereof also containing unreacted starting materials, solvents, products of side reactions, and/or other undesired materials in which the crude terephthalic acid is filtered from that dispersion to partially separate it from the other materials contained therein by filtration to produce a crude terephthalic acid filter cake, and then dissolving that filter cake in a desired selective crystallization solvent at an elevated temperature to form a solution. Purified terephthalic acid is crystallized from that solution by reducing the pressure and temperature thereof and is separated from the solvent following crystallization.

In accordance with still another aspect of the invention, a method and apparatus are provided for producing purified terephthalic acid from crude terephthalic acid by dissolving the crude terephthalic acid in a desired selective crystallization solvent at an elevated temperature to form a first solution. First stage purified terephthalic acid is crystallized from that first solution at a reduced temperature, and preferably at a reduced pressure also. The first stage purified terephthalic acid is separated from the solvent solution of other impurities and redissolved in the desired selective crystallization solvent at an elevated temperature to form a second solution. This second solution is crystallized at a reduced pressure and temperature to form a second stage purified terephthalic acid and the second stage purified terephthalic acid is separated from the second solution.

In accordance with yet another aspect of the invention, crude terephthalic acid is synthesized by contacting paraxylene with oxygen in an oxidizer reaction. The crude terephthalic acid is withdrawn from the oxidizer and separated grossly from the side products of the reaction, and unreacted starting materials. The separated crude terephthalic acid is then dissolved in a desired selective crystallization solvent at an elevated temperature and crystallized from it as purified terephthalic acid at a reduced pressure and temperature. More than one stage of dissolving in a desired selective crystallization solvent at an elevated temperature followed by crystallization at a reduced pressure and temperature, with accompanying separation and washing of the crystallized purified terephthalic acid, may be performed.

From the foregoing, it can be seen that an object of the present invention is to provide an improved method and apparatus for producing purified terephthalic acid of a purity desired for use in forming polyester resin and other products, at an economically attractive rate, and at operating conditions of reduced severity which require a lower capital investment and simplified processing. The manner in which these and other objects of the invention are attained may be learned by consideration of the detailed description of the invention which follows, together with the accompanying drawings.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF EMBODIMENTS

I. Process Description

Figure 1:
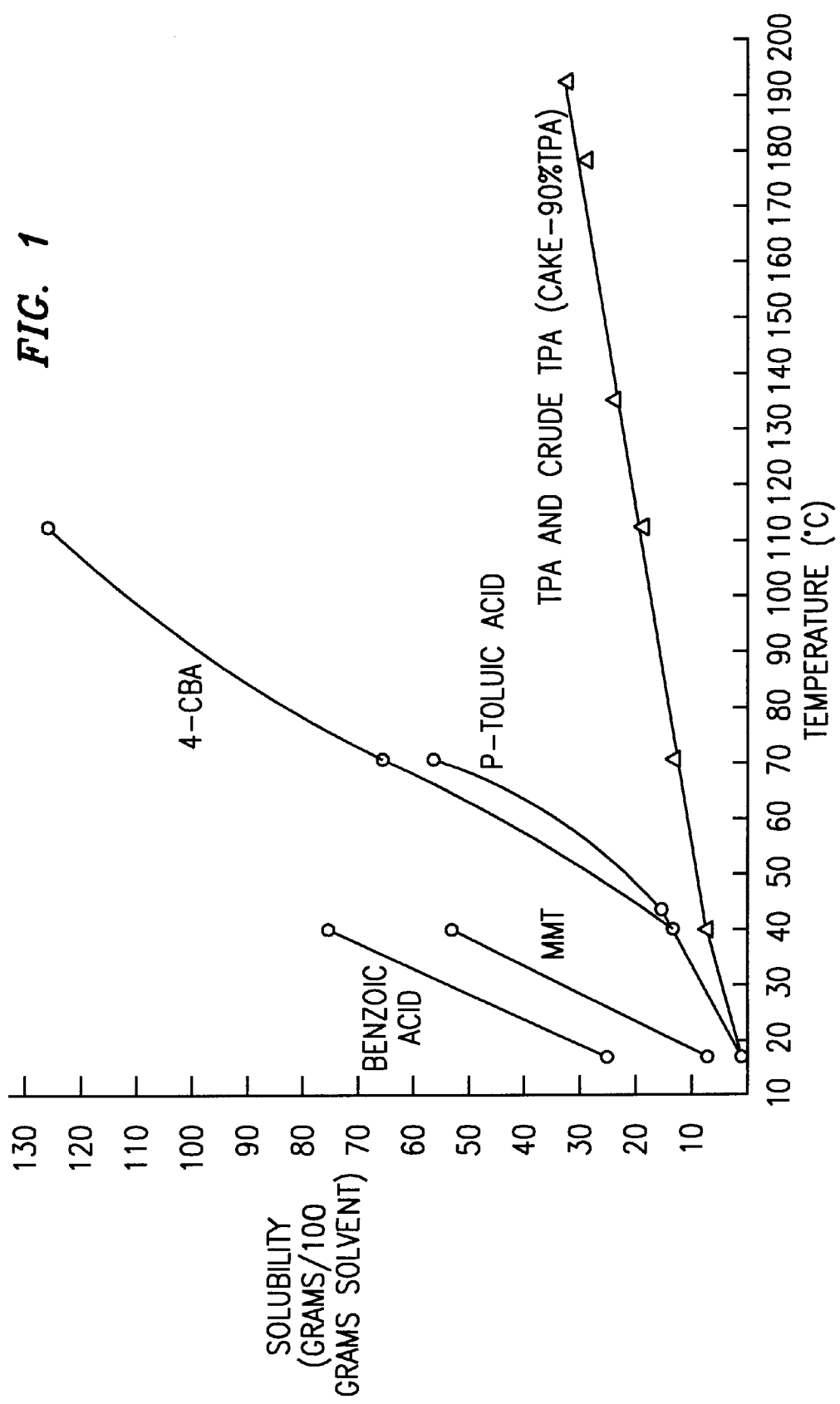
FIGS. 1 and 2 are plots of solubility versus temperature curves for terephthalic acid and for impurities or side reaction products commonly associated with crude terephthalic acid in NMP and DMAC, respectively.
Figure 2:
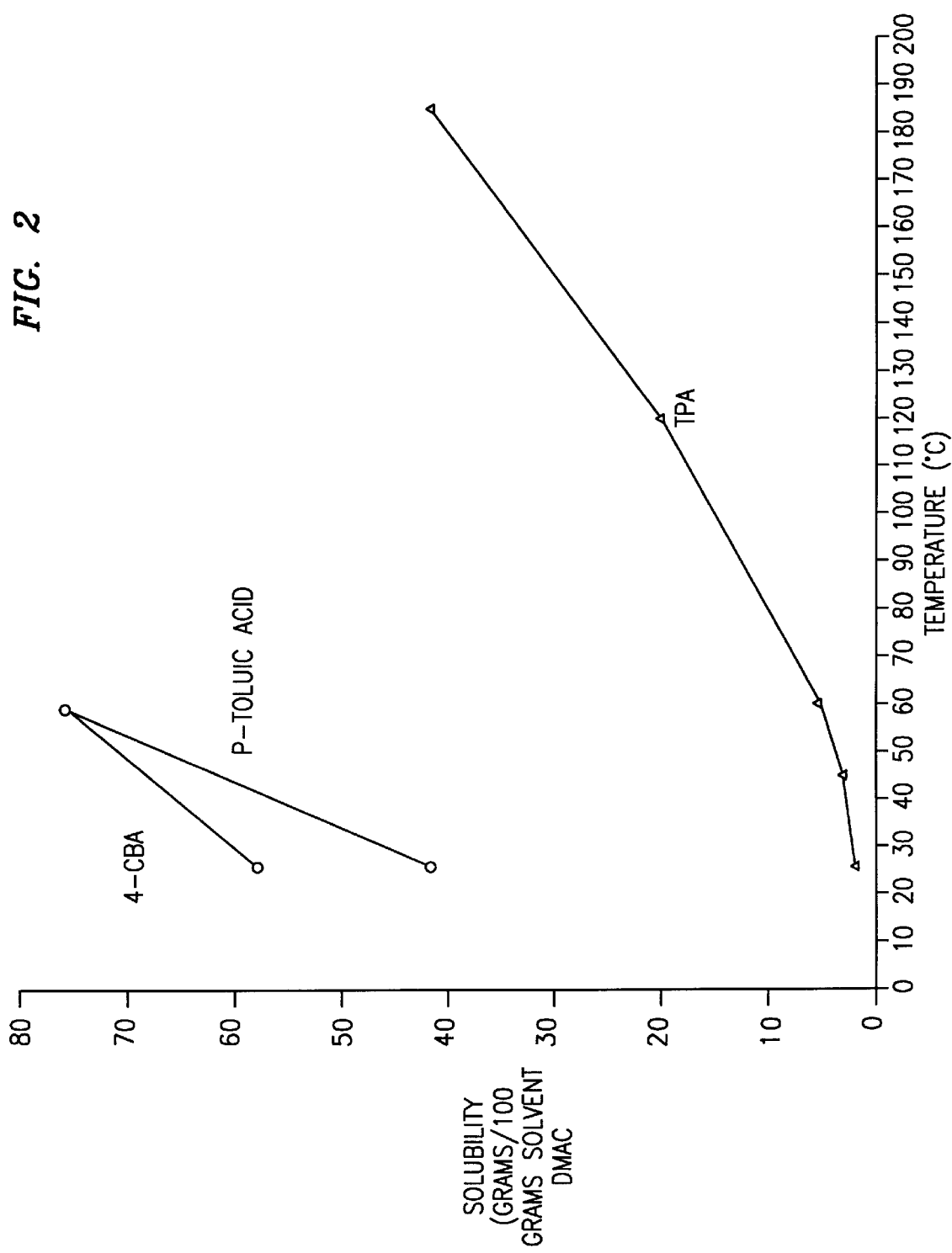

The present invention relates to the development of a new PTA manufacturing technology. Compared to the current widely used PTA technology, this technology provides a substantially lower capital investment in new PTA plant construction, as well as lower costs of plant operation. It also provides means for current DMT plants to co-produce PTA, to strengthen their competitiveness against newer PTA plants.

Process Summary

The success of this process is based on the development of a low pressure, low temperature, non-aqueous, highly selective crystallization technology. The crystallization technology can purify the crude terephthalic acid (TA) with purity as low as from between about 70% (from the oxidizer) and about 98+% in the first-stage crystallizer, and about 99.99+% in the second-stage crystallizer. This allows the TA oxidizer to be operated at much lower severity than those of widely used prior art processes. No acetic acid (as solvent/diluent) or bromine-catalyst initiator is needed in the oxidizer in accordance with the present invention. The selective crystallization solvent used in the crystallization process is non-aqueous, thermally stable, non-toxic (environmentally safe), non-corrosive, and commercially available.

When carrying out the method according to the present invention, employing NMP or DMAC as the selective crystallization solvent, the present inventors have demonstrated TA purity levels of up to 99.9+wt % after a first crystallization process, and up to 99.99+wt % after a second crystallization process. In particular, Table 1 illustrates the recovery of 99.95 wt % pure TA after the first crystallization process and 99.997 wt % pure TA after the second crystallization process, from crude TA (89.89 wt % TA).

TABLE 1

| Crystallization | 1st Crystallization | 2nd |
|---|---|---|
| (a) Weight of TA: | 56.34 grams | 31.81 grams |
| (b) Weight of Crystallization Solvent: | 400.02 grams | 248.38 grams |
| (c) Saturation Temperature: | 60° C. | |
| (d) Crystallization Temperature: | 15° C. (one hour) | |
| (1) Crude TA Product Composition: | | | | | |

| Benzoic | p-Toluic | 4-CBA | TA | Others |
|---|---|---|---|---|
| 0.39 wt % | 4.49 wt % | 2.49 WT % | 89.89 WT % | 274 WT % |

(2) First Crystallization Product

| | | | |
|---|---|---|---|
| 35 ppm | 143 ppm | 359 ppm | 99.95 wt % Not Detected |

(3) Second Crystallization Product

| | | | |
|---|---|---|---|
| <20 ppm | <20 ppm | <10 ppm | 99.997 + wt % |

Table 2 illustrates the recovery of 99.90wt % pure TA after the first crystallization process and 99.9933wt % pure TA after the second crystallization process from crude TA (89.89wt % TA) by increasing both the saturation temperature and the crystallization temperature.

TABLE 2

| Crystallization | 1st Crystallization | 2nd |
|---|---|---|
| (a) Weight of TA: | 138.08 grams | 70.15 grams |
| (b) Weight of Crystallization Solvent: | 685.30 grams | 247.46 grams |
| (c) Saturation Temperature: | 110° C. | 105° C. |
| (d) Crystallization Temperature: | 40° C. | 40° C. |

(1) Crude TA Product Composition:

| Benzoic | p-Toluic | 4-CBA | TA | Others |
|---|---|---|---|---|
| 0.39 wt % | 4.49 wt % | 2.49 wt % | 89.89 wt % | 2.74 wt % |

(2) First Crystallization Product (Recovery: 56.5 wt %)

| Benzoic | p-Toluic | 4-CBA | TA | Others |
|---|---|---|---|---|
| 28 ppm | 367 ppm | 390 ppm | 99.90 wt % | 229 ppm |

(3) Second Crystallization Product (Recovery: 47.5 wt %)

| | | | | |
|---|---|---|---|---|
| <10 ppm | <19 ppm | 25 ppm | 99.9933 wt % | 13 ppm |

Table 3 illustrates the recovery of 99.9960wt % pure TA (single crystallization process) from crude TA (98.99wt % TA). In addition, each of benzoic, p-Toluic, 4-CBA, MMT and other impurities were at less than 10 ppm.

TABLE 3

| (a) | Weight of TA: | 152.67 grams |
|---|---|---|
| (b) | Weight of Crystallization Solvent: | 786.19 grams |
| (c) | Saturation Temperature: | 100° C. |
| (d) | Crystallization Temperature: | 40° C. |

(1) Crude TA Product Composition:

| Benzoic | p-Toluic | 4-CBA | TA | MMT | Others |
|---|---|---|---|---|---|
| <10 ppm | <10 ppm | 18 ppm | 98.99 wt % | 303 ppm | 0.98 wt % |

(2) Crystallization Product (Recovery: 50.2 wt %)

| | | | | | |
|---|---|---|---|---|---|
| <10 ppm | <10 ppm | <10 ppm | >99.9960 wt % | <10 ppm | <10 ppm |

Table 4 illustrates the recovery of 99.63wt % pure TA (single crystallization process) from crude TA (83.91 wt % TA) on a large scale basis.

TABLE 4

| (a) | Weight of TA: | 1760 grams |
|---|---|---|
| (b) | Weight of Crystallization Solvent: | 6162 grams |
| (c) | Saturation Temperature: | 160° C. |
| (d) | Crystallization Temperature: | 50° C. |

(1) Crude TA Feed Product Composition:

| Benzoic | p-Toluic | 4-CBA | TA | Others |
|---|---|---|---|---|
| 1.03 wt % | 4.79 wt % | 5.03 wt % | 83.91 wt % | 5.24 wt % |

(2) Crystallization Product (Recovery: 24.3 wt %)

| | | | | |
|---|---|---|---|---|
| 38 ppm | 852 ppm | 0.23 wt % | 99.63 wt % | 500 ppm |

Table 5 illustrates the recovery of 99.92 wt % pure TA (single crystallization process) from crude TA (79.79 wt % TA) on a large scale basis.

TABLE 5

| (a) | Weight of TA: | 1700 grams |
|---|---|---|
| (b) | Weight of Crystallization Solvent: | 5928 grams |
| (c) | Saturation Temperature: | 160° C. |
| (d) | Crystallization Temperature: | 45° C. |

(1) Crude TA Feed Product Composition:

| Benzoic | p-Toluic | 4-CBA | TA | Others |
|---|---|---|---|---|
| 1.59 wt % | 5.19 wt % | 7.61 wt % | 79.79 wt % | 5.81 wt % |

(2) Crystallization Product (Recovery: 31.5 wt %)

| | | | | |
|---|---|---|---|---|
| 10 ppm | 203 ppm | 446 ppm | 99.92 wt % | 184 ppm |

Table 6 illustrates the recovery of 99.15 wt % pure TA (single crystallization process) from crude TA (83.90 wt % TA) on a large scale basis at a higher saturation temperature of 190° C.

TABLE 6

| (a) | Weight of TA: | 1965 grams |
|---|---|---|
| (b) | Weight of Crystallization Solvent: | 5684 grams |
| (c) | Saturation Temperature: | 190° C. |
| (d) | Crystallization Temperature: | 40° C. |

(1) Crude TA Feed Product Composition:

| Benzoic | p-Toluic | 4-CBA | TA | Others |
|---|---|---|---|---|
| 1.23 wt % | 5.25 wt % | 6.34 wt % | 83.90 wt % | 3.28 wt % |

(2) Crystallization Product (Recovery: 48.9 wt %)

| | | | | |
|---|---|---|---|---|
| — | 0.14 wt % | 0.61 wt % | 99.15 wt % | 0.1 wt % |

Table 7 illustrates the recovery of 99.9915 wt % pure TA from crude TA (98.50 wt % TA) on a large scale basis. The supersaturation of the crystallization mixture resulted in the formation of substantially larger TA crystals than those crystals resulting from the processes summarized above. As would be understood by one skilled in the art, the sizes of TA crystals are an important consideration with respect to separation thereof from solvents and impurities.

TABLE 7

| (a) | Weight of TA: | 2333 grams |
|---|---|---|
| (b) | Weight of Crystallization Solvent: | 5698 grams |
| (c) | Saturation Temperature: | 160° C. |
| (d) | Crystallization Temperature: | 45° C. |

(1) Crude TA Feed Product Composition:

| Benzoic | p-Toluic | 4-CBA | TA | Others |
|---|---|---|---|---|
| 198 ppm | 0.15 wt % | 1.23 wt % | 98.50 wt % | 989 ppm |

(2) Crystallization Product (Recovery: 69.7 wt %)

| | | | | |
|---|---|---|---|---|
| <10 ppm | 26 ppm | 38 ppm | 99.9915 wt % | 11 ppm |

Table 8 demonstrates the recovery of 99.45 wt % pure TPA (single crystallization process) from crude TPA (82.92 wt % TPA), using N,N-dimethyl acetamide (DMAC) as the crystallization solvent. The 4-CBA content was reduced from 6 wt % to 3276 ppm. The range of the operating temperature was very moderate (from 45 to 120° C.).

TABLE 8

Purifying "TPA" with N,N-Dimethyl Acetamide by Crystallization
1. N,N-dimethylacetamide used: 1,000.0 grams
   Crude TPA used: 291.5 grams
   N,N-dimethylacetamide for cake wash: 800 ml
   Purified TPA recovered: 135.6 grams (not including losses due to solids handling and sampling)

| Sample | Benzoic | PTA | 4-CBA | TPA | Unknown |
|---|---|---|---|---|---|
| Crude TPA (wt %) | 5.25 | 6.01 | 4.59 | 82.92 | 1.23 |
| Purified TPA (ppm) | 689 | 3276 | 1519 | 99.45* | 13 |

*weight percent
2. Method:
(a) The mixture was heated to 120° C. in an agitated and jacketed flask to dissolve the solids, and the mixture was held at the temperature for one hour.
(b) The mixture was then cooled to 45° C. in one hour.
(c) The cooled slurry was then filtered in a separatory funnel under vacuum to separate the mother liquor from the cake.
(d) The cake was washed once in the separatory funnel with the solvent to remove the residual mother liquor in the cake. The wash was carried out at room temperature.
(e) The wet solid was soaked over night with D.I. water at room temperature and then washed three times with D.I. water in a separatory funnel.
(f) The solids were dried over night at 180° C.

As has been discussed, important aspects of this invention are related to the discovery of methods to crystallize terephthalic acid (TA) from organic solution where the solvent tends to form an organic salt with TA. The salt is normally formed from cooling the solution of an organic solvent or a mixture of organic solvents, which solution is saturated with TA at higher temperatures. However, crystal structure of the salt is destroyed when it is washed with water or other solvents to remove the solvent in the crystal. The washed crystals become very fine powders which are very difficult to filter and wash in order to remove the impurities in the trapped mother liquor and the residual solvent.

According to this invention, the solution of an organic solvent (or mixture of organic solvents) saturated with TA and impurities such as 4-carboxybenzaldehyde (4-CBA), p-toluic acid, etc., is fed to a crystallizer maintained at a lower pressure (or under vacuum) to allow the solvent (or solvent mixture) to flash instantaneously in a continuous or batch manner. Then, the solids (nuclei) generated from solvent flashing are allowed to grow for a certain period of time at the reduced pressure and temperature. It is desirable to subject the saturated solution to a number of solvent flash operations in the same crystallizer or in several crystallizers connected in series, each at a different reduced pressure (or vacuum), to generate higher TA recovery and larger TA crystals. It has been found, surprisingly, that the structure of the crystals produced from this method is not adversely affected by washing with water or other solvents which have significant solubility of the crystallization solvent (or mixture of solvents) or by vacuum drying the crystals to remove solvent. Consequently, it appears that there was no salt formation or at least the salt formation was minimized so that washing with water or other solvent which can dissolve the crystallization solvent or vacuum drying did not change the size and shape of the TA crystals.

As previously mentioned, organic solvents useful in this invention include, but are not limited to, N-methyl pyrrolidone (NMP), N-ethyl pyrrolidone, N-mercaptoethyl pyrrolidone, N-methyl thiopyrrolidone, N-hydroxyethyl pyrrolidone, 1,5-dimethyl pyrrolidone, N-methyl piperidone, N-methyl caprolactam, N-formyl morpholine, morpholine, N,N-dimethyl formamide, N,N-dimethyl acetamide, N-formyl piperidine, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), and N-hydroxyalkyl-2-pyrrolidone (such as N-hydroxyethyl-2-pyrrolidone).

In order to remove the residual solvent trapped in the crystals from the final TA product, the washed TA crystals are preferably fed to a high temperature soaker where water is used to partially or completely dissolve the TA crystals.

The following examples illustrate the principles and features of the invention.

EXAMPLE 1

Cooling Crystallization 9761 g of NMP was added to a jacketed crystallizer provided with agitation together with 3028 g of TA. This mixture was heated to 180° C. under atmospheric pressure until all of the TA was dissolved.

The mixture was then subjected to surface cooling by circulating a cooling medium through the jacket until a temperature of 45° C. was reached. Then after 15 minutes, the slurry was filtered to separate the solids from the mother liquor, and the cake was washed with room temperature pure NMP to displace all the mother liquor from the cake.

A sample was taken from the cake for observation under a microscope. The crystals had a bar-like shape and a size in the range of 120–150 microns.

In order to remove the solvent from the cake, the cake had to be washed with water or other suitable solvents which have high solubility of the solvent. Hot water at 80° C. was used to wash the cake. However, the bar-like crystals in the cake were completely destroyed by water and changed into fine powders which looked more like precipitates than crystals produced by a crystallization process. These fine precipitates are extremely difficult to wash and handle and the residual solvent removal is complicated.

EXAMPLE 2

Flashing Crystallization

The same sample preparation of NMP and TA as in the previous example was used, except that the mixture was also, prior to the cooling step, subject to a flashing removal of solvent by reducing the pressure from atmospheric to 125 mmHg of vacuum. In this way, some solvent was vaporized out and condensed through a cooler so the temperature of the mixture dropped from 180° C. to 147° C. The amount of solvent flashed out created a super-saturation condition so the TA dissolved in NMP crystallizes into the solid phase.

Although the flashing step is done instantaneously, crystallization of TA requires some time to take place, so the mixture was kept agitated for 30 minutes to form the nuclei and permit them to grow, thus forming a slurry. The slurry was filtered to separate the solids from the liquid phase, washed with pure NMP at room temperature and observed under a microscope. The crystal shape was globular instead of bar-like, as it was when using the previous cooling crystallization method, and very uniform in size but smaller—about 40–60 microns.

Then the cake was washed with hot water at 80° C. and, surprisingly, the globular-like crystals were not affected by water washing (their shape and size were not changed). These globular-like crystals have a very high filtration rate and effectively rinsing them is much easier.

EXAMPLE 3a

Crystal Growth

To promote crystal growth, the experiment, as in the preceding example, was repeated except that 6174 g of NMP and 1952 g of terephthalic acid were used.

Also, the flash pressure was 120 mmHg instead of 125 mmHg and the temperature was 145° C. Then, the mixture was flashed a second time at 40 mmHg, as described in the preceding example, and the temperature dropped to 110° C. Thus, more terephthalic acid crystallized. The crystal shape was globular-like and the size was increased to 60–80 microns.

EXAMPLE 3b

The experiment as in Example 3a was repeated except that 7490 g of NMP and 2325 g of terephthalic acid were used. Also, a different pressure profile was followed and two more flashes were added:

| | |
|---|---|
| first flash: | 150 mmHg @ 154° C. |
| second flash: | 80 mmHg @ 135° C. |
| third flash: | 40 mmHg @ 117° C. |

Observation under a microscope showed that the crystal shape was globular and the size improved significantly. The final sample contained crystals in the range of 120–150 microns.

EXAMPLES 4a AND 4b

Flash/Vaporizing Crystallization

The experiment as in Example 3b was repeated except that the temperature of the hot oil circulation through the jacket was kept 5–10° C. above the crystallizer temperature in a way that some vaporization of the solvent occurred at the same time of the flashing. This procedure resulted in more solvent flashed/vaporized and a lower temperature profile which increases the recovery of the crystals:

| FLASH No. | EXAMPLE 3b | EXAMPLE 4a | EXAMPLE 4b |
|---|---|---|---|
| First | 154° C. | 155° C. | 145° C. |
| | 150 mmHg | 150 mmHg | 150 mmHg |
| | 755 ml of solvent removed by flashing | 1328 ml of solvent removed by flashing | 1660 ml of solvent removed by flashing |
| Second | 135° C. | 135° C. | 130° C. |
| | 80 mmHg | 80 mmHg | 80 mmHg |
| | 696 ml of solvent removed by flashing | 473 ml of solvent removed by flashing | 580 ml of solvent removed by flashing |
| Third | 117° C. | 110° C. | 115° C. |
| | 40 mmHg | 40 mmHg | 40 mmHg |
| | 248 ml of solvent removed by flashing | 110 ml of solvent removed by flashing | 340 ml of solvent removed by flashing |
| Fourth | 101° C. | 90° C. | 95° C. |
| | 20 mmHg | 20 mmHg | 20 mmHg |
| | 135 ml of solvent removed by flashing | 155 ml of solvent removed by flashing | 430 ml of solvent removed by flashing |

When observed under a microscope, the crystals looked globular-like in shape as described for Example 2 above.

EXAMPLE 5

In this example, the 4-CBA rejection characteristics of the flash crystallization method was compared with that of crystallization by cooling alone.

Flash Crystallization

The crystallizer was charged with 31 g TA/100 g solvent. 4-CBA was added to start with a concentration based on solids of around 2%. The mixture was heated to 185° C. and agitated until most of the crystals dissolved. Some crystals may not have dissolved and these became seeds for crystal growth. The oil bath was set to 155° C. The first vacuum (150 mmHg) was pulled to remove around 15–20% of the liquid in about 15 minutes. Next, the flash vacuum was pulled to 80 mmHg and 6–8% of the remaining liquid was removed within 5 minutes. In the third flash, 6–8% of the solvent was removed with a vacuum of 40 mmHg requiring about 6–7 minutes. In the fourth flash, 12% of the solvent was removed with a vacuum of 20 mmHg requiring about 10–15 minutes. Then the mother liquor was cooled to 50° C. as quickly as possible, taking about 30 minutes. The crystals were then removed from the flask and filtered using a Buchner funnel and side arm flask. About 200 g of 50° C. solvent was then poured over to wash the crystals. The crystals were then put in a pressure filter and dried by passing nitrogen for 30 minutes at 40 psi. The final crystals were analyzed for 4-CBA content, giving a result of 500 ppm.

Cooling Crystallization

The crystallizer was charged with 31 g TA/100 g solvent. 4-CBA was added to start with a concentration based on solids of 2%. The mixture was heated to 185° C. and agitated until most of the crystals dissolved. Some crystals may not have dissolved and these became seeds for crystal growth. Cooling of the mix was started to crystallize the TA from the solution. The cooling rate was 2° C./min to a final temperature of 50° C. The crystals were then removed from the flask and filtered using a Buchner funnel and side arm flask. About 200 g of 50° C. solvent was then poured over to wash the crystals. The crystals were then put in a pressure filter and dried by passing nitrogen for 30 minutes at 40 psi. These final crystals were analyzed for 4-CBA content, giving a result of about 500 ppm.

The experiments show that the flash and cooling crystallization processes have substantially the same rejection capability for 4-CBA.

According to the invention, a preferred embodiment of the process is divided into five sections:

(1) Oxidation Section:

In this section, p-xylene is oxidized according to the following main reactions:

| | | |
|---|---|---|
| (a) | p-xylene + oxygen -> terephthalic acid + water | |
| (b) | p-xylene + oxygen -> p-toluic acid + water | |
| (c) | p-xylene + oxygen -> 4-carboxybenzaldehyde (4-CBA) + water | |

The oxidizer residence time is approximately five hours. Since the oxidizer effluent will contain up to about 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by an air sparger and by external circulation. Depending on the thoroughness of the p-xylene washing step at the filter (discussed below), the terephthalic acid (TA) in the solid can vary from between about 55% and about 90+%.

(2) Crystallization Section:

(A) First Crystallization

After filtration, the solids from the oxidizer effluent are mixed with the mother liquor and the solvent wash liquid from the second-stage crystallizer and with additional crystallization solvent. The mixed slurry is dissolved in a slurry tank at a predetermined temperature, preferably at from between about 140° C. and about 200° C.. The saturated solution is transferred to a holding tank to remove p-xylene through evaporation. The saturated solution is then fed to a first-stage batch crystallizer to recover purified TA by flash evaporation of solvent at reduced pressure and/or cooling. After the crystallization step, the crystallizer content is then dropped to a product holding tank and is pumped continuously to a filter (or centrifuge) to collect the solids to be recrystallized in the second-stage crystallizer for further purification.

(B) Second Crystallization

The solids generated from the first crystallizer filter are redissolved in a feed dissolver with the crystallization solvent for the second-stage crystallizer at a predetermined condition, such as at a temperature of from between about 140° C. and about 200° C. The saturated solution is pumped to the second-stage crystallizer for crystal growth and recovery, again, by flash evaporation of solvent at reduced pressure and/or cooling. Then, the crystallizer content is dropped to a holding tank for filtration before being sent to the soaker. In the filtration step, the solid (cake) is first washed by the crystallization solvent to displace mother liquor remaining in the cake. The solid is then washed by a low-boiling solvent to displace the crystallization solvent in the cake and subsequently dried to remove the final liquid from the PTA product. The crystallization solvent alternatively can be displaced by drying the solid using a vacuum dryer and subjecting the cake to a soaking process. The soaking process comprises partially or completely dissolving the TA in a solvent, crystallizing the product in water at a high temperature and high pressure to remove residual solvent trapped in the crystals, and recrystallizing, filtering and drying the TA cake.

(3) Mother Liquor/Solvent Recovery Section:

The mother liquor from the first crystallizer filter is transferred to a solvent recovery column to recover the crystallization solvent from the column overhead. The impurities, such as, but not intended to be limited to, p-toluic acid, benzoic acid, 4-carboxybenzaldehyde (4-CBA), and the like, are recovered from the bottom of the column. In order to make sure the column bottom slurry can be transferred back to the oxidizer, a high-boiling diluent is preferably added to the reboiler.

II. Detailed Process Description and Example

The present inventions will be described in terms of the production and recovery of terephthalic acid (TA) from the air oxidation of p-xylene in the presence of a solution of components of catalysis in dimethyl terephthalate (DMT) or in a benzoic acid-water solvent system. The oxidizer temperature is preferably between about from 150° C. and about 250° C. and the pressure is from between about 5 and about 30 kg per cm$^2$. Since the oxidizer effluent will contain up to 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by air sparging and external circulation. In the preferred form of the process manganese acetate and cobalt acetate in aqueous solution are fed to the oxidizer to catalyze the oxidation reactions.

The effluent from the oxidizer at about 160° C. is transferred and filtered via a first filter to separate the solid from mother liquor (filtrate). During filtering, the solid cake is washed with p-xylene which is heated from 30° C. to 100–150° C. The mother liquor is transferred to a first holding tank. The cake washing liquid is removed separately from the first filter to a second holding tank.

The washed cake is dropped into a first slurry tank to mix with the following streams: (1) NMP or DMAC (selective crystallization solvent) wash liquor (heated from 45 to 100–150° C.); (2) mother liquor (heated from 50 C. to 100–150° C.); and (3) NMP or DMAC (heated from 45° C. to 100–150° C.).

The above mixture is then transferred from the bottom of the first slurry tank to a first dissolver tank. The content in the first dissolver tank is then heated indirectly from 100–150° C. to 140–200° C. by a hot oil heating coil in the first dissolver tank. About 75% of the p-xylene and 100% of the sparging nitrogen in the mixture is vaporized from the first dissolver tank and removed. Sparging nitrogen is added to the first dissolver tank to assist the removal of p-xylene. Vapor streams from the first dissolver tank and a crude crystallizer are combined into a stream, condensed by a cooler, and sent to a first storage tank. The bottom effluent from the first dissolver tank is transferred to the crude crystallizer batchwise.

The batch content in the crude crystallizer is reduced in pressure in the manner described above with concurrent removal of flashed solvent and cooled from 140–200° C. to 10–20° C. by an external cooler, to generate the desired super-saturation for TA crystals to grow. During pressure reduction, heat may be added to the batch to effect further solvent removal. To improve the crystal size distribution and solid recovery, crystal seeding may be helpful. At the conclusion of a batch crystallization cycle, the slurry is dropped into a third holding tank and transferred to a second filter where it is filtered at a continuous rate.

During filtering at the second filter, NMP or DMAC is used to wash the cake in the second filter. The mother liquor plus NMP or DMAC wash are combined to be fed to a crystallization solvent recovery column. The washed cake is dropped into a second dissolver tank where it is mixed with NMP or DMAC to form the super-saturated feed for a pure crystallizer. NMP or DMAC is heated from 45° C. to 140–200° C. and is fed to the second dissolver tank.

The content of the second dissolver tank is transferred batchwise to the pure crystallizer where the pressure is reduced in the manner described above and the temperature is cooled from 140–200° C. to 30–60° C. to induce TA crystal growth. The cooling is provided by circulating the crystallizer content through an external cooler. Again, to improve the crystal size distribution and crystal recovery, crystal seeding may be helpful. At the end of the batch cycle, the slurry is dropped from the pure crystallizer into a feed tank for the third filter.

The slurry is continuously fed to the third filter. The mother liquor from the first filter is transferred to a fourth holding tank. The cake is initially washed with NMP or DMAC at 45° C. to displace the remaining mother liquor from the cake, and then the cake is washed with the low-boiling displacement solvent, such as water, to displace NMP or DMAC from the cake or, alternatively, sent to a vacuum dryer. The NMP or DMAC wash (from a crystallization solvent storage tank) and the displacement solvent are then added to the third filter. The NMP or DMAC wash liquid is sent to the first slurry tank, while the displacement solvent is transferred to a fifth holding tank.

The washed cake from the third filter is passed through a wash column or multistage contactor and counter-current water is added to remove the crystallization solvent. The slurry from the wash column or contactor is then fed to the soaker where the temperature is raised to from between about 150–250° C. to remove trapped solvent from the crystals. The slurry is finally filtered and dropped to a product dryer where water (moisture) in the cake is removed by heating and purging with a counter-current flow of heated nitrogen. The dried PTA product is removed from the dryer and is stored in the product bin.

The bottom stream from the fifth holding tank (mixture of NMP and displacement solvent), together with the liquid from the wash column or multi-stage contactor, is transferred through a heater (to heat the stream from 25° C. to 80–120° C.) to a displacement solvent evaporator. The displacement solvent vapor from the overhead of the displacement solvent evaporator is condensed and sent to the displacement solvent tank. The bottom stream from the displacement solvent evaporator is split into two streams: one stream to the vent pot and a second stream to the crystallization solvent tank.

The mother liquor and NMP or DMAC wash from the second filter are transferred to the crystallization solvent tank and then are fed to the NMP or DMAC recovery column. This stream is heated from 15–25° C. to 130–170° C. before entering the recovery column. The overhead vapor is condensed and sent to a condensate pot. A part of the condensate at 160–220° C. is returned to the recovery column as the reflux. The rest of the overhead product from recovery column is sent to a crystallization solvent check tank. From the crystallization solvent check tank, the regenerated NMP or DMAC is pumped to a NMP or DMAC storage tank.

In order to make sure the slurry in the recovery column reboiler can be transferred back to the oxidizer, high-boiling diluent, such as benzoic acid or DMT, is added to the reboiler. The slurry plus the high-boiling diluent is withdrawn from the bottom of the recovery column and is sent back to the oxidizer.

Figure 3:
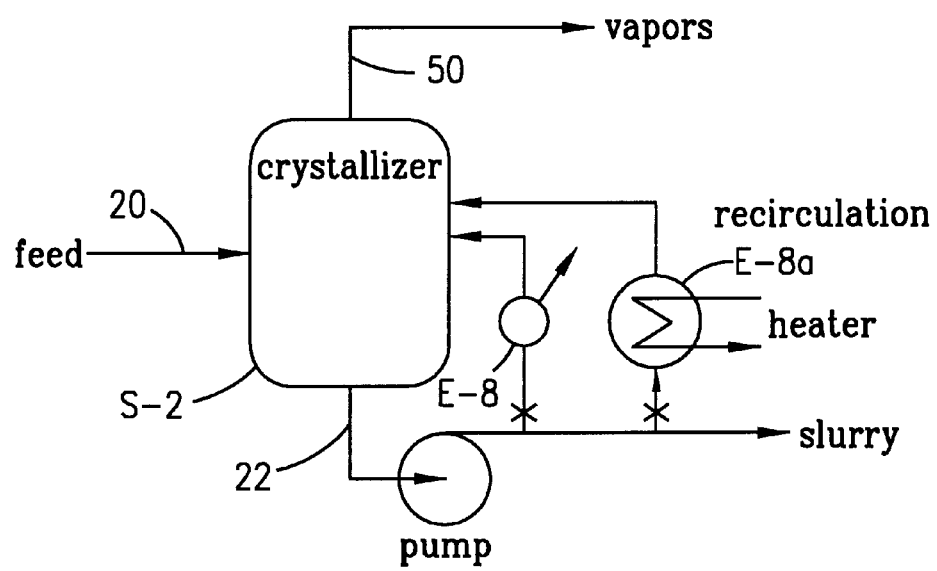
FIG. 3 is a simplified elevational diagram of a crystallizer which may be used in the practice of the invention.

In FIG. 3, there is shown an arrangement of a crystallizer S-2 useful for the practice of the embodiment of the invention in which heat is added to the crystallizing acid mixture during the times when the pressure is being reduced to flash solvent. As shown in FIG. 3, crystallizer S-2 is there provided with both a cooling recirculation circuit with exchanger E-8, and a heating recirculation circuit with heater E-8a. Heat is applied to the mixture by heater E-8a during flashing, and cooling is applied to the mixture at other times by exchanger E-8. Flashed solvent (e.g. NMP or DMAC) is removed through line 50 for recycling to the recovery column, and the pressure reduction vacuum is also applied to the crystallizer through line 50.

Although a preferred embodiment of the method and apparatus of the present invention has been illustrated in the accompanying drawings and described in the foregoing detailed description, it will be understood that the invention is not limited to the embodiment disclosed, but is capable of numerous rearrangements, modifications and substitutions without departing from the spirit of the invention as set forth and defined by the following claims.

What is claimed is:

1. An apparatus for purifying crude terephthalic acid from a liquid dispersion thereof also containing impurities selected from unreacted starting materials, solvents, products of side reactions and/or other undesired materials comprising:

means for filtering said dispersion to form a crude terephthalic acid filter cake;

means for dissolving said filter cake in a selective crystallization solvent at an elevated temperature of from between about 140° C. and about 200° C. to form a solution;

means for crystallizing purified terephthalic acid from said solution in said crystallization solvent by reducing the temperature and pressure sufficient to flash evaporate solvent from said terephthalic acid of said solution; and means for separating said crystallized purified terephthalic acid from said solution.

2. An apparatus for producing purified terephthalic acid from crude terephthalic acid comprising:

means for dissolving crude terephthalic acid in a selective crystallization solvent at an elevated temperature of from between about 140° C. and about 200° C. to form a first solution;

means for crystallizing first stage purified terephthalic acid from said first solution at a reduced temperature and pressure sufficient to flash evaporate solvent from said terephthalic acid;

means for separating said crystallized first stage purified terephthalic acid from said solution;

means for redissolving said separated first stage purified terephthalic acid in said selective crystallization solvent at an elevated temperature to form a second solution;

means for crystallizing second stage purified terephthalic acid from said second solution at a reduced temperature and pressure sufficient to flash evaporate solvent from said terephthalic acid; and means for separating said crystallized second stage purified terephthalic acid from said second solution.

3. An apparatus for purifying crude terephthalic acid from a liquid dispersion thereof also containing impurities selected from unreacted starting materials, solvents, products of side reactions and/or other undesired materials, said apparatus comprising:

means for dissolving crude terephthalic acid in NMP or DMAC at a temperature of from between about 140° C. and about 200° C. to form a first solution;

means for crystallizing said dissolved crude terephthalic acid from said first solution at a temperature of from between about 5° C. and about 50° C. and a reduced pressure sufficient to flash evaporate solvent from said terephthalic acid to form first stage purified terephthalic acid;

means for separating said first stage purified terephthalic acid from said first solution by filtration to form a first stage purified terephthalic acid filter cake;

means for washing said separated first stage purified terephthalic acid filter cake with N-methyl pyrrolidone or N,N-dimethyl acetamide;

means for redissolving said first stage purified terephthalic acid filter cake in NMP at a temperature of from between about 140° C. and about 200° C. to form a second solution;

means for crystallizing said redissolved first stage purified terephthalic acid from said second solution at a temperature of from between about 5° C. and about 50° C. and a reduced pressure sufficient to flash evaporate solvent from said terephthalic acid to form second stage purified terephthalic acid;

means for separating said second stage purified terephthalic acid from said second solution by filtration to form a second stage purified terephthalic acid filter cake;

means for washing said second stage purified terephthalic acid filter cake with N-methyl pyrrolidone or N,N-dimethyl acetamide; and means for washing said N-methyl Pyrrolidone washed filter cake with water and means for further treating it by:

(a) drying it; or (b) vacuum drying it, then water soaking it at elevated temperature or contacting it with water in a wash column or multi-stage column, then filtering or centrifuging it;

to provide purified terephthalic acid.

* * * * *

UNITED STATES PATENT AND TRADEMARK OFFICE
CERTIFICATE OF CORRECTION

PATENT NO. : 6,113,866
DATED : September 5, 2000
INVENTOR(S) : Lee et al.

Page 1 of 1

It is certified that error appears in the above-identified patent and that said Letters Patent is hereby corrected as shown below:

Title page,
Item [56], References Cited, U.S. PATENT DOCUMENTS,
Add -- 5,256,817  10/1993  Sikkenga et al  562/487
       5,292,934  3/1994   Sikkenga et al  562/413
       5,304,676  4/1994   Hindmarsh et al 562/414 --

Column 11,
Line 30, add -- fourth flash: 20 mmHg @ 101° C. --

Signed and Sealed this

Fifteenth Day of January, 2002

Attest:

JAMES E. ROGAN
*Attesting Officer*  *Director of the United States Patent and Trademark Office*